US00PP31885P2

(12) United States Plant Patent
Monte-Michielsen

(10) Patent No.: US PP31,885 P2
(45) Date of Patent: Jun. 16, 2020

(54) ***GERANIUM* PLANT NAMED 'TOSTC0258'**

(50) Latin Name: ***Pelargonium* x *hortorum***
Varietal Denomination: TOSTC0258

(71) Applicant: Ball Horticultural Company, West Chicago, IL (US)

(72) Inventor: Fabienne Monte-Michielsen, Brielle (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,949

(22) Filed: Jul. 9, 2019

(51) Int. Cl.
*A01H 5/02* (2018.01)
*A01H 6/42* (2018.01)

(52) U.S. Cl.
USPC ..... Plt./329

(58) Field of Classification Search
USPC ..... Plt./263.1, 324, 329
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Geranium* plant named 'TOSTC0258', characterized by its semi-double type, deep purplish-pink and white colored flowers, medium green-colored foliage with zonation, and vigorous, upright-mounded growth habit, is disclosed.

1 Drawing Sheet

Latin name of genus and species of plant claimed: *Pelargonium* x *hortorum.*

Variety denomination: 'TOSTC0258'.

BACKGROUND OF THE INVENTION

The present invention relates to a new and distinct cultivar of *Geranium* plant botanically known as *Pelargonium* x *hortorum* and hereinafter referred to by the cultivar name 'TOSTC0258'.

The new cultivar originated in a controlled breeding program in Hendrik-Ido-Ambacht, The Netherlands during July 2014. The objective of the breeding program was the development of heat-tolerant *Geranium* cultivars with semi-double type flowers having attractive flower coloration, and a vigorous, upright-mounded growth habit.

The new *Geranium* cultivar is the result of cross-pollination. The female (seed) parent of the new cultivar is the proprietary *Pelargonium* x *hortorum* breeding selection coded TA0530, not patented, characterized by its semi-double type, medium pink-colored flowers, medium green-colored foliage having zonation, and moderately vigorous, upright-mounded growth habit. The male (pollen) parent of the new cultivar is Trend Hot Pink 'Hanna', also sold as Dynamo Hot Pink 'ToscaQ488', not patented, characterized by its semi-double type, dark hot pink colored flowers, medium green-colored foliage having zonation, and moderately vigorous, upright-mounded growth habit. The new cultivar was discovered and selected as a single flowering plant within the progeny of the above stated cross-pollination during August 2015 in a controlled environment in Hendrik-Ido-Ambacht, The Netherlands.

Asexual reproduction of the new cultivar by terminal stem cuttings since August 2015 in Hendrik-Ido-Ambacht, The Netherlands, and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'TOSTC0258' as a new and distinct cultivar of *Geranium* plant:

1. Semi-double type, deep purplish-pink and white colored flowers;
2. Medium green-colored foliage with zonation; and
3. Vigorous, upright-mounded growth habit.

Plants of the new cultivar differ from plants of the female parent primarily in having increased growth vigor. Plants of the new cultivar differ from plants of the male parent primarily in having a lighter pink flower color and increased growth vigor.

Of the many commercially available *Geranium* cultivars, the most similar in comparison to the new cultivar is Big Ezee Pink 'Duebezpinimp', U.S. Plant Pat. No. 27,852. However, in comparison, plants of the new cultivar differ from plants of 'Duebezpinimp' in at least the following characteristics:

1. Plants of the new cultivar have a flower color that is slightly darker pink than plants of 'Duebezpinimp';
2. Plants of the new cultivar have smaller diameter inflorescences than plants of 'Duebezpinimp'; and
3. Plants of the new cultivar are shorter than plants of 'Duebezpinimp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'TOSTC0258'. The plants were approximately 3 months old and grown in 4.5-inch pots for approximately 10 weeks in a greenhouse in West Chicago, Ill.

DETAILED BOTANICAL DESCRIPTION

Figure 1:
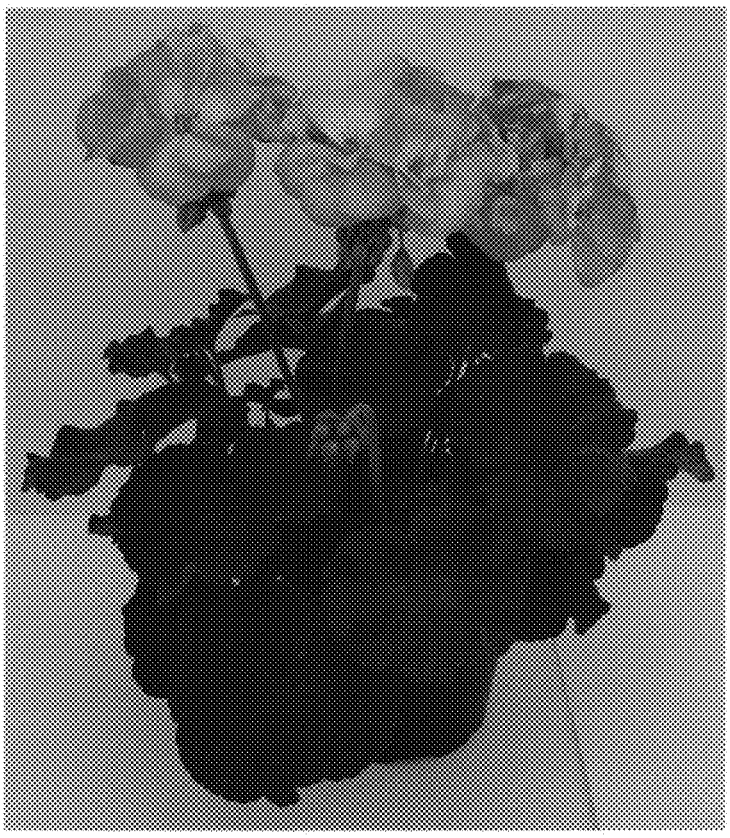
FIG. 1 illustrates a side view of the overall growth and flowering habit of 'TOSTC0258'.
Figure 2:
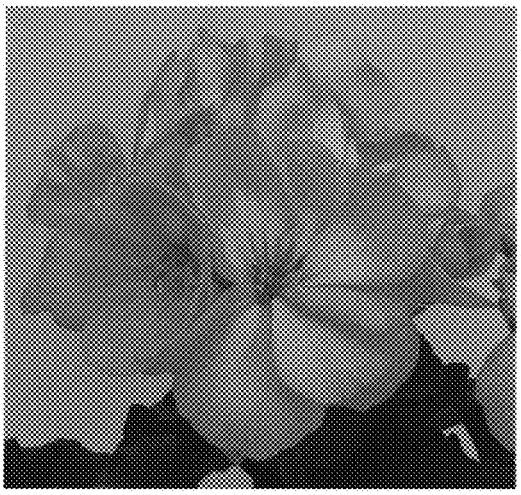
FIG. 2 illustrates a close-up view of an individual umbel of 'TOSTC0258'.
Figure 3:
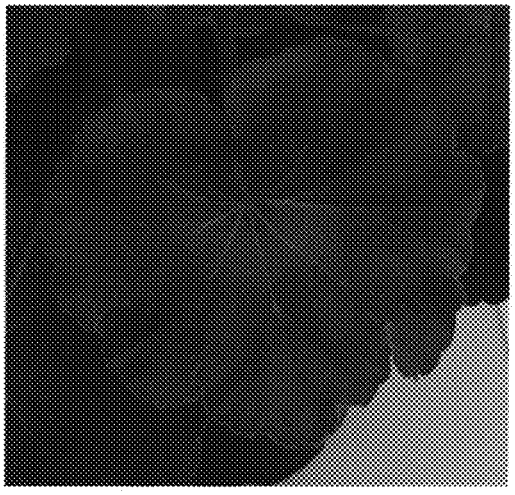
FIG. 3 illustrates a close-up view of an individual leaf of 'TOSTC0258'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2019 under natural light conditions in West Chicago, Ill.

The following descriptions and measurements describe approximately 3-month old plants produced from cuttings from stock plants and grown in a glass-covered greenhouse under conditions comparable to those used in commercial practice. The plants were grown in West Chicago, Ill. in 4.5-inch pots for approximately 10 weeks utilizing a soilless growth medium. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Pelargonium* x *hortorum* 'TOSTC0258'.

Parentage:

*Female parent*.—Proprietary *Pelargonium* x *hortorum* breeding selection coded TA0530, not patented.

*Male parent*.—Trend Hot Pink 'Hanna', also sold as Dynamo Hot Pink 'ToscaQ488', not patented.

Propagation:

*Type cutting*.—Terminal stem.

*Time to initiate roots*.—Approximately 9 to 12 days.

*Time to produce a rooted cutting*.—Approximately 24 to 28 days.

*Root description*.—Fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Vigorous, upright-mounded.

*Size*.—Height from soil level to top of plant plane: Approximately 24.5 cm. Height from soil level to top of foliage: Approximately 14.5 cm. Width: Approximately 28.0 cm.

*Branching habit*.—Freely basal branching. Quantity of main branches per plant: Approximately 3.

*Branch*.—Strength: Strong. Length: Approximately 7.0 cm. Diameter: Approximately 6.0 mm. Length of central internode: Approximately 1.2 cm. Texture: Densely pubescent with a mixture of glandular and nonglandular hairs. Gland color: 17D and colorless, transparent. Color of young and mature stem: 146C.

Foliage description:

*General description*.—Quantity of leaves per lateral branch: Approximately 8. Fragrance: Moderate. Form: Simple. Arrangement: Opposite.

*Leaves*.—Aspect: Petiole is at an acute angle to stem, blade is primarily perpendicular to stem. Shape: Reniform. Margin: Bicrenate, palmately lobed, moderately wavy. Apex: Obtuse. Base: Cordate. Venation pattern: Palmate. Length of mature leaf: Approximately 7.5 cm. Width of mature leaf: Approximately 9.0 cm. Texture of upper and lower surfaces: Densely pubescent with a mixture of glandular and nonglandular hairs. Gland color: Colorless, transparent. Color of upper surface of young foliage: Closest to 137B with a faint overlay of NN137A on zonal area of approximately outer two thirds of leaf, venation of 146C. Color of lower surface of young foliage: 147B with venation of 146D. Color of upper surface of mature foliage: Closest to 137A with an overlay of NN137A on zonal area of approximately outer two thirds of leaf, venation of 146C. Color of lower surface of mature foliage: Closest to 147B with venation of 146D.

*Petiole*.—Length: Approximately 6.0 cm. Diameter: Approximately 2.5 mm. Texture: Densely pubescent with a mixture of glandular and nonglandular hairs. Gland color: 17D and colorless, transparent. Color: 146B.

Flowering description:

*Flowering habit*.—'TOSTC0258' is freely flowering under outdoor growing conditions with substantially continuous blooming from spring through autumn and year-round in greenhouse environment.

*Lastingness of individual flower on the plant*.—Approximately 12 to 14 days.

Inflorescence description:

*General description*.—Type: Umbel, semi-spherical. Positioned above foliage. Quantity of fully open umbels per plant: Approximately 2. Quantity of developing umbels per plant: Approximately: 2. Fragrance: None detected. Length or height: Approximately 6.0 cm. Width: Approximately 8.5 cm. Quantity of fully open flowers per inflorescence: Approximately 12.

*Peduncle*.—Strength: Strong. Aspect: Erect. Length: Approximately 14.0 cm. Diameter: Approximately 4.0 mm. Texture: Densely pubescent with a mixture of glandular and nonglandular hairs. Gland color: 17D and colorless, transparent. Color: 146B.

Flower description:

*General description*.—Type: Semi-double.

*Bud*.—Rate of opening: Generally takes 3 to 4 days for bud to progress from first color to fully open flower.

*Bud just before opening*.—Shape: Elliptic. Length: Approximately 1.1 cm. Width: Approximately 8.0 mm. Sepal texture: Densely pubescent with a mixture of glandular and nonglandular hairs. Gland color: Colorless, transparent. Petal texture: Glabrous. Petal color: N57D.

*Corolla*.—Shape: Round. Diameter: Approximately 5.0 cm. Depth: Approximately 2.5 cm.

*Petals*.—Quantity: Approximately 7 to 9 petals and 1 to 2 irregularly-shaped petaloids per flower. Shape:

Obovate. Appearance: Dull. Margin: Entire. Apex: Obtuse. Base: Attenuate. Length of upper petals: Approximately 2.7 cm. Width of upper petals: Approximately 2.4 cm. Length of lower petals: Approximately 2.5 cm. Width of lower petals: Approximately 2.3 cm. Texture of upper and lower surfaces: Glabrous. Color of upper surface of upper petals when fully open: Approximately lower half of NN155D with upper half of N66C, venation of N66B at base. Color of lower surface of upper petals when fully open: NN155D with an overlay of N66D, venation of N66C. Color of upper surface of lower petals when fully open: N66C with a small area of NN155D at base. Color of lower surface of lower petals when fully open: NN155D with an overlay of N66D, venation of N66C.

*Calyx*.—Shape: 5-pointed star. Diameter: Approximately 2.1 cm.

*Sepals*.—Quantity per flower: Approximately 5, fused at base. Shape: Lanceolate. Margin: Entire. Apex: Acuminate. Length of upper sepal: Approximately 1.1 cm. Width of upper sepal: Approximately 4.0 mm. Length of lower sepals: Approximately 1.2 cm. Width of lower sepals: Approximately 3.0 mm. Texture of upper surface: Glabrous. Texture of lower surface: Densely pubescent with a mixture of glandular and nonglandular hairs. Gland color: Colorless, transparent. Color of upper and lower surfaces: 146D tinted with 185A at base.

*Pedicel*.—Strength: Strong. Aspect: Acute angle to peduncle. Length: Approximately 2.3 cm. Diameter: Approximately 2.0 mm. Texture: Densely pubescent with a mixture of glandular and nonglandular hairs. Gland color: Colorless, transparent. Color: 146D tinted with 185A.

*Reproductive organs*.—Androecium: Quantity of mature stamens: Approximately 6 to 8 per flower. Anther shape: Oblong. Anther length: Approximately 2.0 mm. Anther color: 71B. Filament length: Approximately 7.0 mm. Filament color: NN155D with an overlay of 71A near anther. Pollen amount: Moderate. Pollen color: 32A. Gynoecium: Pistil quantity: 1 per flower. Pistil length: Approximately 1.0 cm. Stigma shape: 5-branched. Stigma length: Approximately 2.0 mm. Stigma color: 186A. Style length: Approximately 3.0 mm. Style color: 186A. Ovary length: Approximately 5.0 mm. Ovary texture: Densely pubescent. Ovary color: 145A.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'TOSTC0258', substantially as herein illustrated and described.

* * * * *